(12) United States Patent
Van Dorpe et al.

(10) Patent No.: US 9,909,992 B2
(45) Date of Patent: Mar. 6, 2018

(54) OPTICAL SPECTROMETER WITH MATCHED ÉTENDUE

(71) Applicant: IMEC VZW, Leuven (BE)

(72) Inventors: Pol Van Dorpe, Spalbeek (BE); Peter Peumans, Herfelingen (BE)

(73) Assignee: IMEC VZW, Leuven (BE)

(*) Notice: Subject to any disclaimer, the term of this patent is extended or adjusted under 35 U.S.C. 154(b) by 11 days.

(21) Appl. No.: 15/119,055

(22) PCT Filed: Feb. 28, 2015

(86) PCT No.: PCT/EP2015/054225
§ 371 (c)(1),
(2) Date: Aug. 15, 2016

(87) PCT Pub. No.: WO2015/128503
PCT Pub. Date: Sep. 3, 2015

(65) Prior Publication Data
US 2016/0356720 A1    Dec. 8, 2016

(30) Foreign Application Priority Data

Feb. 28, 2014    (EP) .................................... 14157397

(51) Int. Cl.
*G01J 3/30*    (2006.01)
*G01N 21/65*    (2006.01)
(Continued)

(52) U.S. Cl.
CPC ........... *G01N 21/65* (2013.01); *A61B 5/0066* (2013.01); *A61B 5/1455* (2013.01);
(Continued)

(58) Field of Classification Search
CPC .................. G01N 21/65; G01N 33/49; G01N 2201/06113; G01N 2201/0633;
(Continued)

(56) References Cited

U.S. PATENT DOCUMENTS

| 5,011,284 A | 4/1991 | Tedesco et al. |
| 7,925,069 B2 | 4/2011 | Ortyn et al. |
| (Continued) | | |

FOREIGN PATENT DOCUMENTS

WO    WO 1997/02475 A1    1/1997

OTHER PUBLICATIONS

PCT International Search Report and Written Opinion, PCT International Application No. PCT/EP2015/054225, dated Jun. 3, 2015, 10 pages.

*Primary Examiner* — Hina F Ayub
(74) *Attorney, Agent, or Firm* — McDonnell Boehnen Hulbert & Berghoff LLP

(57) ABSTRACT

The present disclosure relates to systems, methods, and sensors configured to characterize a radiation beam. At least one embodiment relates to an optical system. The optical system includes an optical radiation guiding system. The optical radiation guiding system includes a collimator configured to collimate the radiation beam into a collimated radiation beam. The optical radiation guiding system also includes a beam shaper configured to distribute power of the collimated radiation beam over a discrete number of line shaped fields. A spectrum of the collimated radiation beam entering the beam shaper is delivered to each of the discrete number of line shaped fields. The optical system further includes a spectrometer chip. The spectrometer chip is configured to process the spectrum of the collimated radiation beam in each of the discrete number of line shaped fields coming from the beam shaper.

20 Claims, 12 Drawing Sheets

(51) Int. Cl.

| | |
|---|---|
| *A61B 5/00* | (2006.01) |
| *A61B 5/145* | (2006.01) |
| *A61B 5/1455* | (2006.01) |
| *G01J 3/02* | (2006.01) |
| *G01J 3/36* | (2006.01) |
| *G01J 3/44* | (2006.01) |
| *G01J 3/26* | (2006.01) |
| *G01N 33/49* | (2006.01) |
| *G01J 3/12* | (2006.01) |

(52) U.S. Cl.
CPC .......... *A61B 5/14532* (2013.01); *A61B 5/443* (2013.01); *G01J 3/021* (2013.01); *G01J 3/0205* (2013.01); *G01J 3/0208* (2013.01); *G01J 3/0227* (2013.01); *G01J 3/0256* (2013.01); *G01J 3/0264* (2013.01); *G01J 3/0291* (2013.01); *G01J 3/26* (2013.01); *G01J 3/36* (2013.01); *G01J 3/44* (2013.01); *G01N 33/49* (2013.01); *A61B 2562/0233* (2013.01); *A61B 2562/0238* (2013.01); *G01J 2003/1213* (2013.01); *G01N 2201/0633* (2013.01); *G01N 2201/0636* (2013.01); *G01N 2201/06113* (2013.01)

(58) Field of Classification Search
CPC .......... G01N 2201/0636; A61B 5/0066; A61B 5/14532; A61B 5/1455; A61B 5/443; A61B 2562/0233; A61B 2562/0238; G01J 3/0205; G01J 3/0208; G01J 3/021; G01J 3/0227; G01J 3/0256; G01J 3/0264; G01J 3/0291; G01J 3/26; G01J 3/36; G01J 3/44; G01J 2003/1213
USPC .......................................... 356/311
See application file for complete search history.

(56) References Cited

U.S. PATENT DOCUMENTS

| | | |
|---|---|---|
| 2007/0127019 A1 | 6/2007 | Zribi et al. |
| 2009/0310135 A1* | 12/2009 | Bockstaele ............... G01J 3/02 356/328 |
| 2012/0226118 A1 | 9/2012 | Delbeke et al. |
| 2012/0275189 A1 | 11/2012 | Laine et al. |

* cited by examiner

OPTICAL SPECTROMETER WITH MATCHED ÉTENDUE

CROSS-REFERENCE TO RELATED APPLICATION

The present application is a national stage entry of PCT/EP15/054225 filed Feb. 28, 2015, which claims priority to European Patent Application No. 14157397.2 filed on Feb. 28, 2014, the contents of each of which are hereby incorporated by reference.

FIELD OF THE INVENTION

The invention relates to techniques for non-invasive measuring of analytes. In particular, the present invention relates to techniques for non-invasive measuring of analytes in skin or other tissue using Raman spectroscopy. In addition to non-invasive measurements of analytes in the human body, the method can also be used to measure the properties of produce, fluids, textile, etc.

BACKGROUND OF THE INVENTION

Raman spectroscopy is a known optical technique for identifying molecules. The identification is based on vibrational information specific to chemical bonds and symmetry of molecules. The technique provides a fingerprint by which molecules may be uniquely identified. Consequently, Raman spectroscopy can be used as a qualification and quantification technique for detecting analytes of interest in a sample.

As optical, non-destructive technique, Raman spectroscopy also be used for identifying targets of interest in medical applications, for example identifying molecules in the skin of an individual and to estimate the total number of such molecules in the volume probed. One application that has been envisaged in the past is the sensing of glucose in a living creature.

Nevertheless, as for most optical techniques, the response signal when measuring glucose is very limited. To monitor glucose in a living creature, a small signal variation is to be measured while a significant amount of background signal is present. Therefore it is important that a detector based on Raman spectroscopy has a high sensitivity.

Raman scattering will lead to a light signal that is isotropic, i.e. emitting in all directions. The spectrometer needs to capture light propagating in all angles as much as possible. In addition, since light scatters readily in skin, the light that is available at the skin surface is spread out over a substantial area (1 mm2 or more, depending on the illumination scheme used). This creates the challenge of collecting light over all angles and a large area, i.e. a large étendue (proportional to area times solid angle), which is a fundamental challenge in optics since spectrometers that are able to collect and process a light signal with a large étendue are challenging to design and build.

Moreover due to the differences in the local geometry of the skin (e.g. different thicknesses and microstructure of the various layers that make up skin) for different positions on the skin as well as for different individuals, it is difficult to quantify the concentration of a particular analyte without performing calibration steps for each individual separately. Therefore, to obtain a reproducible technique, calibration is performed systematically. This is typically a time consuming and cumbersome process that limits the applicability of the Raman technique for doing accurate routine non-invasive measurements of important analytes such as glucose, cholesterol, ethanol, etc.

Together with the required high sensitivity and the need for calibration, another requirement typically is the ease of use of the sensor for the user. For example in case of glucose sensing, sensing typically needs to be performed at least a couple of times a day. Conventional Raman systems typically are large optical systems and cannot be used for convenient day-to-day glucose monitoring. Efforts have been made to miniaturize optical Raman systems. Some suggestions have been made in the past to use an implantable sensor, an example thereof being described in U.S. patent application Ser. No. 13/415,392. Whereas implantable sensors can be easy to use and even allow continuous monitoring once they have been implanted, such implantable sensors require accurate packaging while maintaining access to the tissue or fluids to be measured and also require a surgical step for implanting them.

There is still a need for a good Raman based optical sensor, with high sensitivity, good accuracy and with good ease of use for the user.

SUMMARY OF THE INVENTION

It is an object of some embodiments to provide an optical system for detecting a light spectrum whereby the optical system has a high coupling factor with the light source. Some embodiments have an optical system that is able to accept a large étendue of the light source. Some embodiments have a matched étendue. Some embodiments allow a cheap, compact and sensitive Raman based device to be obtained, allowing determination of the concentration of analytes in tissue.

The above objective is accomplished by a method and device according to some embodiments.

In one aspect, disclosure relates to an optical system for characterizing a radiation beam, the spectrometer comprising an optical radiation guiding system comprising a collimator for collimating the radiation beam into a collimated radiation beam, and a beam shaper for distributing the power of the collimated radiation beam over a discrete number of line shaped fields, and a spectrometer chip wherein spectrometer chip is adapted for processing the radiation in a discrete number of line shaped fields coming from the beam shaper. The optical system may be a spectrometer.

By increasing the number of waveguides of the optical system, the overall spectrometer étendue can be increased to match the source étendue. Some embodiments allow a very large number of incoupling gratings to be realized. The collimated radiation beam may be directed substantially in a single direction with a maximum angular spread of 20°.

According to certain embodiments, the beam shaper thereby is configured such that the spectrum of the collimated radiation beam entering the beam shaper is being delivered to each of the discrete number of line shaped fields. In other words, the beam shaper is configured to not split the collimation radiation beam into spectrally different sub-beams for the different discrete line shaped fields, but rather is configured for splitting the collimation radiation beam in power over the different line shaped fields. The beam shaper may distribute the collimation radiation beam equally over the discrete line shaped fields, the whole spectrum thus being distributed to each of the discrete line shaped fields. The beam shaper thus may be adapted for performing a power distribution without inducing a spectrum distribution (the spectral components are not split over the different line shaped fields.

The system processes the different line shaped fields spectrally after the line shaped fields have been split by the beam shaper.

The beam shaper may have a wedge shape. Some embodiments of allow collimated radiation entering the wedge to be spread out over a large area while allowing to keep the height of the system limited. The latter can improve the wearability of the device.

The collimator and the beam shaper may be arranged so that the beam shaper can receive radiation via a wedge entrance area being the short side of the wedge. Some embodiments allow a system with limited height to be obtained, resulting in improved wearability.

The beam shaper may be shaped so that radiation incident orthogonally at a wedge entrance area is guided directly to the wedge exit area without first being reflected at another surface of the wedge.

At least part of the collimator may have a 3D parabolic or hyperbolic shape. Some embodiments allow accurate beam collimation to be obtained.

The collimator may have an entrance point and is shaped so as to fold an irradiation beam between the entrance point and an output of the collimator. Some embodiments allow a compact optical system to be provided.

The beam shaper may comprise an exit area for directing the radiation to the discrete number of line shaped fields, the exit area having a waved or stepped pattern. Some embodiments allow the light refracted on the exit area of the wedge and the refraction to be location dependent.

The waved or stepped pattern may comprise a plurality of first segments and a plurality of second segments, the second segments interconnecting the first segments, neighbouring first segments being positioned at a distance shorter than the length of the first segments and oriented substantially parallel with an orthogonal direction to an entrance area of the beam shaper.

The second segments may be curved. Some embodiments allow radiation which is refracted by a second segment to be focused on a line of the spectrometer chip. The first segments may have an equal length and/or the second segments may have an equal length and shape.

The spectrometer chip may comprise a plurality of detection channels, each detection channel may comprise an incoupling grating, an outcoupling grating, a spectrally dependent transmission system wherein the incoupling grating may be coupled with the outcoupling grating through the spectrally dependent transmission system and wherein the incoupling gratings of the different detectors may be arranged on a discrete number of lines. The incoupling grating and/or outcoupling grating may be shared over a number of detectors. Some embodiments allow a distribution of the incoupling gratings over a discrete number of lines to increase the number of single mode waveguides as more space is available compared to only one line of incoupling gratings. Some embodiments allow the wedge to be designed such that, when light from a light source is distributed by the wedge over a discrete number of line shaped fields, the spacing and orientation of the line shaped fields arriving at the spectrometer chip corresponds with the spacing and orientation of the incoupling gratings. This results in a high coupling factor between the light source and the spectrometer chip.

The spectrally dependent transmission system may be a Fabry-Perot system.

A first rejection filter may be present between the collimator and the beam shaper for rejecting an excitation radiation. According to certain embodiments, a second rejection filter may be present between the beam shaper and the spectrometer chip and/or a third rejection filter may be implemented in the spectrally dependent transmission system using Bragg grating.

The optical system may be integrated in a wristband. Some embodiments allow for, by wearing the wristband, a good contact between the entrance of the collimator and the skin to be realized. Some embodiments allow a good wearability of the sensing system to be obtained.

The disclosure also relates to the use of an optical system as described above as a glucose sensor. Some embodiments allow a glucose level of a patient or a variation therein to be measured without disturbing the patient too much, i.e. that a glucose measurement can be done without substantially hampering patient comfort. During use, the measured spectra may be correlated with a reference glucose spectrum for increasing the signal to noise ratio. Some embodiments allow the signal to noise ratio to be increased if a standard response of a particle or molecule to be detected can be used as reference spectrum.

Embodiments also relate to a detector system wherein the detector system comprises an optical system mounted on an optical printed circuit board and a read-out printed circuit board wherein the read-out printed circuit board is connected with the optical printed circuit board for digitizing the optical signal and/or processing the digitized result. Some embodiments allow the read-out printed circuit board and the optical system to be directly connected reducing the overall noise in the detector system. In some embodiments, the optical system and/or the read-out system may be integrated in a wristband.

The present disclosure also relates to an optical radiation guiding system comprising a collimator for collimating radiation beam into a collimated radiation beam, and a beam shaper for distributing the power of the collimated radiation beam over a discrete number of line shaped fields. The beam shaper thus may be adapted for performing a power distribution without inducing a spectrum distribution (the spectral components are not split over the different line shaped fields.

According to certain embodiments, the beam shaper thereby is configured such that the whole spectrum of the collimated radiation beam is being delivered to each of the discrete number of line shaped fields. In other words, the beam shaper is configured to not split the collimation radiation beam into spectrally different sub-beams for the different discrete line shaped fields, but rather is configured for splitting the collimation radiation beam in power over the different line shaped fields.

Particular aspects are set out in the accompanying independent and dependent claims. Features from the dependent claims may be combined with features of the independent claims and with features of other dependent claims as appropriate and not merely as explicitly set out in the claims.

These and other aspects will be apparent from and elucidated with reference to the embodiment(s) described hereinafter.

Figure 1A:
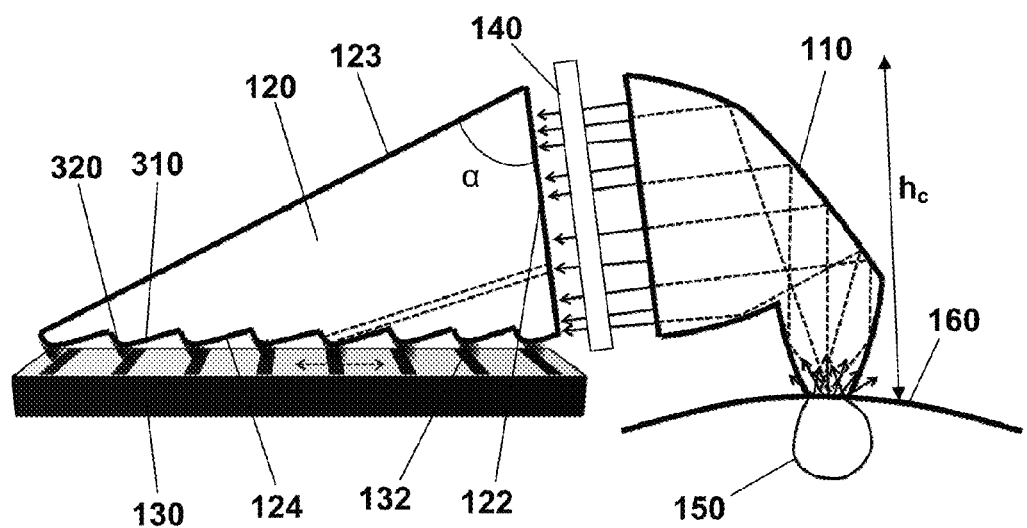
FIG. 1a shows a schematic drawing of an optical system in accordance with example embodiments.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments may be practiced without these specific details. In other instances, well-known methods, structures and techniques have not been shown in detail in order not to obscure an understanding of this description.

Where in embodiments reference is made to "étendue", reference is made to the geometrical extent of light in an optical system. It characterizes how spread out the light is.

Where in embodiments reference is made to "N", reference is made to the total number of waveguides on the chip. In embodiments described herein, N varies between 1,000 and 10,000,000, e.g. between 100,000 and 5,000,000. The number of waveguides is a function of the étendue of the optical signal that need to be measured. The total étendue of the collection of waveguides should ideally exceed the étendue of the light signal that impinges on the chip. Practical considerations such as maximum reticle size and cost of the chip may result in a lower practical optimum. The étendue per waveguide is of the order of $\lambda^2$. So if the light signal has an étendue of 1 mm$^2$, approximately 1,000,000 waveguides are needed to match the étendue of the light signal for $\lambda=1$ µm.

Where in embodiments reference is made to "L", reference is made to the total number of different spectral responses. In embodiments described herein L varies between 50 and 500.

Where in embodiments reference is made to "M", reference is made to the number of repeats. Hereby L is equal to the total number of waveguides N divided by the total number of different spectral responses. In embodiments described herein M varies between 200 and 10000.

In a first aspect, the present invention relates to an optical system for characterizing a radiation beam, e.g. a radiation beam captured after interaction with an object to be characterized.

Embodiments may provide high sensitivity, whereby the étendue of the incoming radiation source is accepted and is substantially maintained in the optical system.

Embodiments can for example be used for identifying molecules (e.g. for glucose quantification in tissue or interstitial fluid under the skin of a person). Embodiments may for example be used for quantifying molecular presence/concentration in heavily scattering objects. For applications that target the skin, this may include e.g. glucose but quantification of other biomolecules also may be performed. In some embodiments, the optical system comprises an optical radiation guiding system comprising a collimator for collimating the radiation beam into a collimated radiation beam. Such a collimate radiation beam may be a radiation beam whereby the spread of the radiation is limited, e.g. may be a radiation beam of radiation with a maximum angular spread of 20°. In certain embodiments, the optical system also comprises a beam shaper for distributing the power of the light coming from the collimator over a discrete number of line shaped fields. The beam shaper thereby is configured such that the spectrum of the collimated radiation beam entering the beam shaper is being delivered to each of the discrete number of line shaped fields. In other words, the beam shaper is configured to not split the collimation radiation beam into spectrally different sub-beams for the different discrete line shaped fields, but rather is configured for splitting the collimation radiation beam in power over the different line shaped fields.

It is to be noticed that prior to entering the beam shaper, the excitation radiation can be filtered partly or fully from the collimated radiation beam.

In some embodiments, the optical system 100 furthermore comprises a spectrometer chip wherein the spectrometer chip is adapted for processing the radiation in a discrete number of line shaped fields coming from the beam shaper. In some embodiments, the étendue is conserved.

By way of illustration, embodiments not being limited thereby, standard and optional features of the optical system will be discussed in more detail. Reference will be made to the drawings, an optical system 100 being shown by way of illustration in FIG. 1a.

In some embodiments, the collimator expands the cross-section of the light beam in exchange for collimation. In certain embodiments, the collimator redirects the radiation from an incoming radiation beam into a single direction with a maximum angular spread of 20°, e.g., 10°. In some embodiments, the exit area of the collimator is between 3 and 80 mm$^2$, e.g., between 5 and 20 mm$^2$, for example 10 mm$^2$. In some embodiments, the entrance area of the collimator is between 0.25 and 10 mm$^2$, e.g., between 0.5 and 2 mm$^2$, for example 1 mm$^2$.

In some embodiments, the collimator may have a 3D parabolic shape. The ratio between the entrance area and exit area may for example equal $$\frac{Area_{exit}}{Area_{entrance}} = \frac{1}{(\sin\theta)^2} = 10$$

Hereby $\theta$ is the angular spread. If $\theta=20°$ the ratio between exit area and entrance area is equal to 10. This illustrates the relation between the expansion of the cross-section of the light beam and the collimation of the light beam.

In some embodiments, the collimator 110 is designed such that, when a radiation beam is provided at the entrance of the collimator 110, the actual beam path is folded, as shown by way of example in FIG. 1a. In certain embodiments, the radiation beam may be folded over an angle between 30° and 150°, e.g. over an angle between 60° and 120°.

In an embodiment, the excitation zone has an étendue of 1 mm$^2$ and is the incoming radiation corresponds with a diffuse source generating 10$^8$ photons/second. In operation, the radiation is firstly collimated by the collimator 110, in a next stage it is distributed over a discrete number of line shaped fields by the wedge 120, after which it is detected by the spectrometer chip 130. This operation is explained for the embodiment illustrated in FIG. 1a. In the embodiment of FIG. 1a the entrance of the collimator 110 has an area of 1 mm$^2$. The radiation at the entrance 150 may correspond with a diffuse source generating not collimated light, stemming from an irradiated tissue or interstitial fluid, e.g. at the skin. The angular spread of the radiation ranges between 0° and 90°, so that the radiation coming out of the diffuse scattering source, e.g. the skin, may be shaped as a full 90 degrees half cone. The radiation at entrance in the illustrative example has a photon flux of 10$^7$-10$^8$ photons/sec. The radiation (e.g. Raman light leaving the skin) goes through a collimator 110 in which the area of the radiation is expanded and the radiation gets collimated. The exit area of the collimator of the system schematically presented in FIG. 1a is 30 mm$^2$ and the angular spread of the outgoing radiation is 10.5°. The radiation leaving the collimator has an étendue of 1.2 mm$^2$. The photon flux at the output of the collimator 110 equals 0.8×10$^8$ photons/sec in the example. The incoming light is oriented and collimated by reflection on the side walls of the collimator. The reflection may be based on total internal reflection or by a metallic coated surface with a high reflectance. The shape typically is optimized for redirecting the radiation and collimating it. The collimation part may be designed such that it resembles or is equal to a compound hyperbolic concentrator or a compound parabolic concentrator. Nevertheless, also other collimator elements based on lenses could be used. In some embodiments, the collimator is limited in height. The height $h_c$ of the collimator in the example of FIG. 1a is about 5 mm.

As indicated above, in some embodiments, a beam shaper 120 is present between the collimator 110 and the spectrometer chip 130. The beam shaper 120 distributes the radiation coming from the collimator 110 over a discrete number of line shaped fields. The radiation coming from the collimator enters the beam shaper at the beam shaper entrance area 122 and leaves the beam shaper at the beam shaper exit area 124. The beam shaper and the collimator are arranged so that collimated radiation is guided directly, or after filtering, towards the entrance region of the beam shaper. The entrance area of the beam shaper thereby may be parallel with the exit area of the collimator. Alternatively the entrance area of the beam shaper may be not parallel with the exit area of the collimator. The entrance area of the collimator shown in FIG. 1a and the exit area of the collimator are not fully parallel. In some embodiments the beam shaper 120 may have the shape of a wedge. Thereby the wedge 120 has a wedge entrance area 122 oriented towards the exit area of the collimator 110 and a wedge exit area 124 oriented towards the spectrometer chip 130. In the embodiment illustrated in FIG. 1a the cross-section of a wedge 120 is shown. The drawing is not at scale.

In at least some embodiments, the radiation, after entering the wedge, will first reflect at the upper area of the wedge 123, thus being reflected downwards to an exit area of the wedge. Through shaping of the exit area, the radiation can then be focused in a detection zone. This principle is shown in FIG. 1a.

Figure 1B:
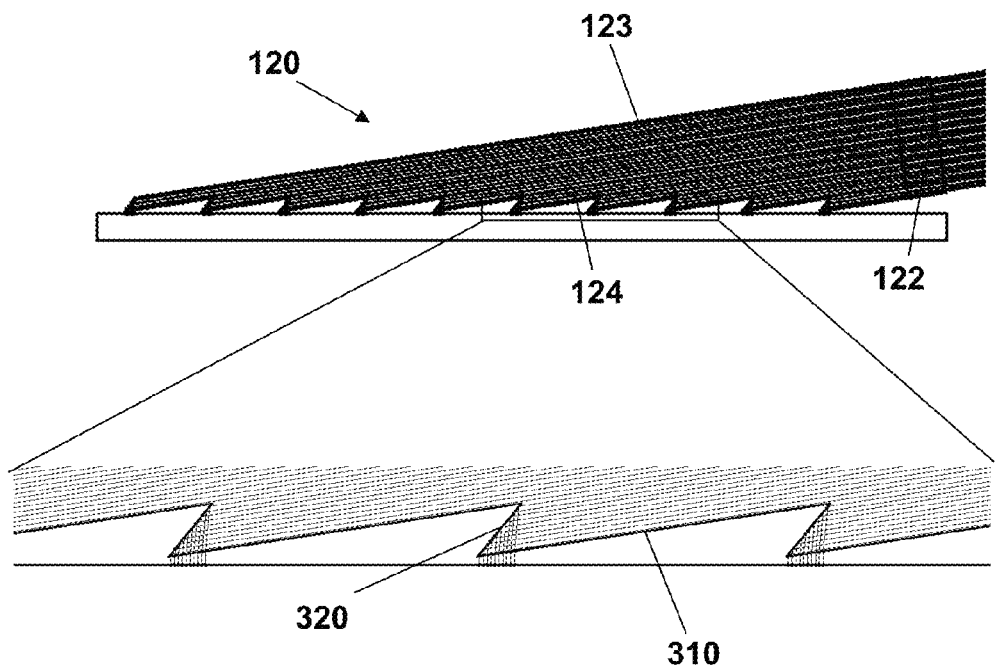
FIG. 1b shows a schematic drawing of an alternative wedge in accordance with example embodiments.

In at least some embodiments, the angle between the wedge entrance area 122 and the upper area of the wedge 123 is 90° so that irradiation entering the wedge perpendicularly to the wedge entrance does not hit the upper edge first but hits the wedge exit area 124 first. As the drawing in FIG. 1b is not at scale, the angle α, which is 90° in the associated embodiment, is not preserved in the drawing of the associated embodiment. The enlarged portion in FIG. 1b illustrates how the reflection of the radiation occurs.

In some embodiments, the wedge exit area 124 has a waved or stepped pattern. In the cross-section orthogonal to the wedge entrance area 122 and the wedge exit area 124 as shown in FIGS. 1a and 1b, a stepped pattern can be seen for the wedge exit area 124. The stepped exit area 124 thereby comprises first segments 310 which in some embodiments may be surfaces oriented orthogonally to the wedge entrance area 122. The distance between neighboring first segments 310 may be smaller than the length of the first segments 310. The stepped shape moreover comprises second segments 320 interconnecting the first segments 310. The second segments 320 may be flat surfaces or curved surfaces. The second segments 320 may be cylindrically shaped surfaces. The waved/stepped exit area of the present example schematically shown in FIG. 1b comprises a plurality of second segments spread over a distance of 20 mm. The radiation is reflected by total internal reflection at the second segments 320 of the wedge exit area 124 towards the first segments and thus towards the spectrometer chip 130. This can be seen in the enlarged portion of FIG. 1b. In some embodiments, the first segments 310 may have an equal shape so that the line shaped fields are equal in width. In some embodiments, the second segments 320 have an equal length and shape. In some embodiments, the width of the line that is illuminated is compatible with two incouplers in the spectrometer chip 130, the two incoupler coupling into two opposite directions.

The area of the wedge exit area 124 in the example schematically illustrated in FIG. 1a equalled 200×10 mm×0.01 mm² =20 mm². The étendue of the light leaving the wedge 120 was π·0.6 mm². The light leaving the wedge 120 has an angular spread 10° and a photon flux of 0.2×10⁸ photons/sec. From this embodiment it can be concluded that the overall collection efficiency can be above 10% and that the étendue is conserved as much as possible. The combination of the large number of input waveguides and the specific light guiding structure thus conserves the etendue as much as possible. If the input is comparted with the output, 60% is reached, while the total photon count is still 20%. As known, the etendue is limited by the smallest etendue of the system, and while the etendue of the totality of the emitted light will increase, the etendue of the light reaching the grating couplers will have decreased, due to the limitations of the optics.

In some embodiments, the optical system 100 also comprises a spectrometer chip 130 wherein the spectrometer chip 130 is enabled for detecting radiation coming from the beam shaper 120. In some embodiments, the spectrometer chip 130 comprises a plurality of detectors 210. Each detector comprises an incoupling grating 220, an outcoupling grating 230, and a spectrally dependent transmission system 240. The incoupling grating 220 is coupled with the outcoupling grating 230 through the spectrally dependent transmission system 240 and the incoupling gratings 220 of the different detectors 210 are arranged on a discrete number of lines. The incoupling gratings 220 typically may be arranged such that they are in line with the line shaped radiation fields created by the beam shaper.

In an embodiment, the spectrometer chip comprises 200 lines wherein radiation is received. The height of the active part of the spectrometer chip equals 20 mm. This corresponds with a distance $d_1$ between the lines of 0.1 mm. Each line in the spectrometer chip comprising around 2000×2 waveguides. In this embodiment the total number of waveguides and incoupling gratings N therefore is equal to 200×2×2000=800,000. Some embodiments allow the spectrometer étendue to be increased because the total number of waveguides can be large because of the spatial heterodynisation. By decreasing the distance $d_1$ between the lines, the total number of lines can be increased even more given the same total height. The spectrometer étendue ε of the incoupling zone equals:

$$\epsilon = N \times \lambda^2 = 2000 \times 2 \times 200 \times (850 \text{ nm})^2 = 0.58 \text{ mm}^2$$

Hereby $\lambda^2 = (850 \text{ nm})^2 = 0.72 = 0.72 \text{ μm}^2$ is the étendue of a waveguide.

In the embodiment described above the spectrometer étendue is up to 0.58 mm² per photonics layer. With denser arrangements of waveguides, larger étendues per photonics layer may be possible. Multiple photonics layers can also be stacked to achieve higher overall étendues.

In the embodiment the width of a line equals 10 mm. In general, the width essentially depends on the output width of the collimator. In some embodiments, the distance between the lines $d_1$ may vary depending on the resolution that is to be obtained. The distance between the lines may be set by the maximum length required to match the spectral resolution of the spectrometer. For the glucose spectrum, one may want to resolve peaks with a width of about 2 to 3 nm. In one example, the distance between the lines may vary between 20 μm and 2 mm, e.g., between 50 μm and 1 mm. In the embodiment the number of different spectral responses L equals 200. Therefore the number of waveguides per spectral type M equals: 800,000/200=4,000, or in other words on average 4,000 waveguides are used per spectrally different output of the spectrometer.

In some embodiments, the spectrally dependent transmission system 140 is a Fabry-Perot system. Other compact structures with spectrally tunable transmission can be used as spectrally dependent transmission system 140. For example: a Mach-Zhender interferometer or a ring resonator, etc. In some embodiments, the signal level is increased when the number of photons at the output of the spectrometer chip 130 is increased. The photon output of the spectrometer chip 130 is proportional to the étendue multiplied with the average photon transmission probability. The étendue per waveguide/incoupling grating 220 is limited. Some embodiments allow a high photon output to be realized using a Fabry-Perot type spectrally dependent transmission system 140.

Figure 13:
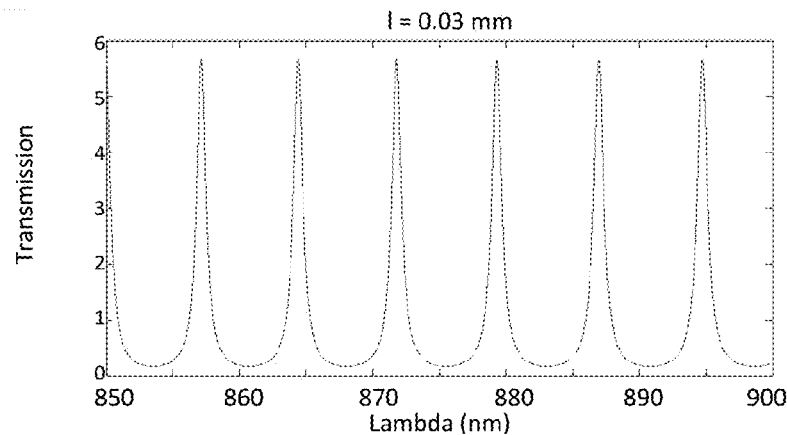
FIG. 13 shows the transmission of a waveguide in accordance with example embodiments.
Figure 14:
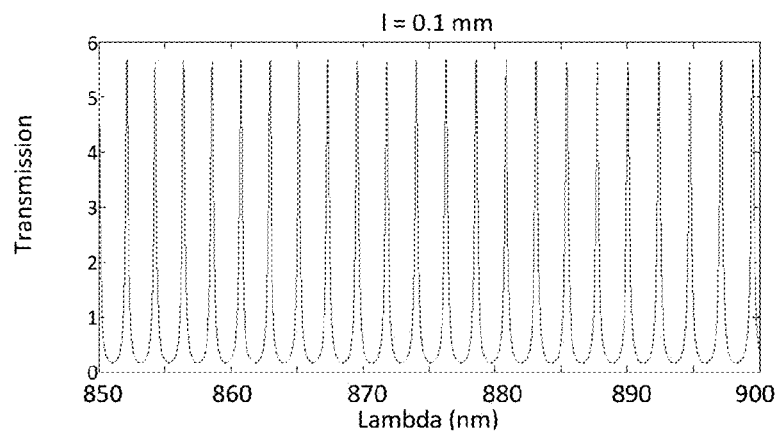
FIG. 14 shows the transmission of a waveguide in accordance with example embodiments.
Figure 15:
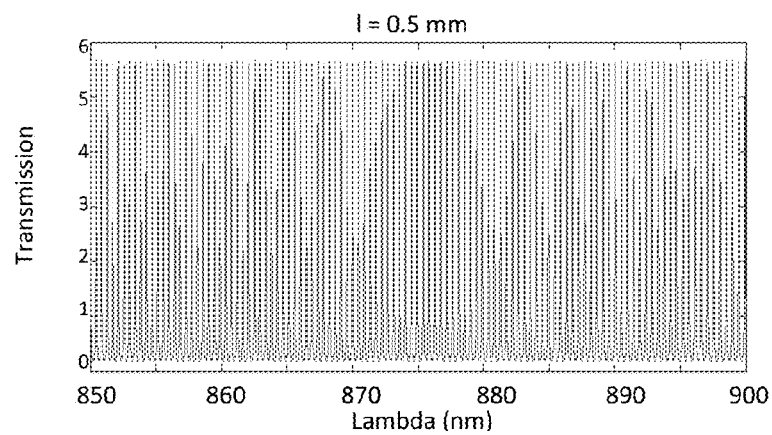
FIG. 15 shows the transmission of a waveguide in accordance with example embodiments.
Figure 16:
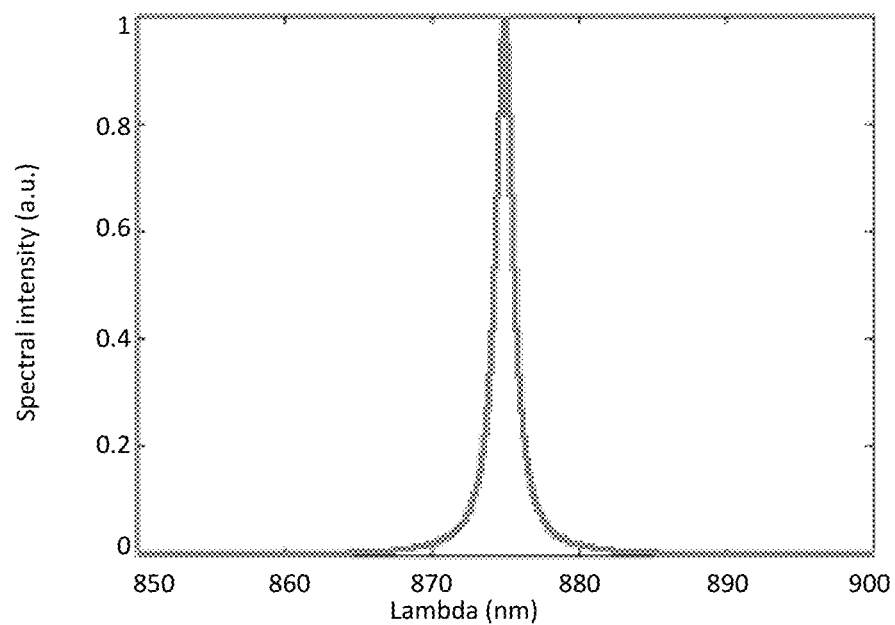
FIG. 16 shows an incoming spectrum as can be processed in a system according to example embodiments.
Figure 17:
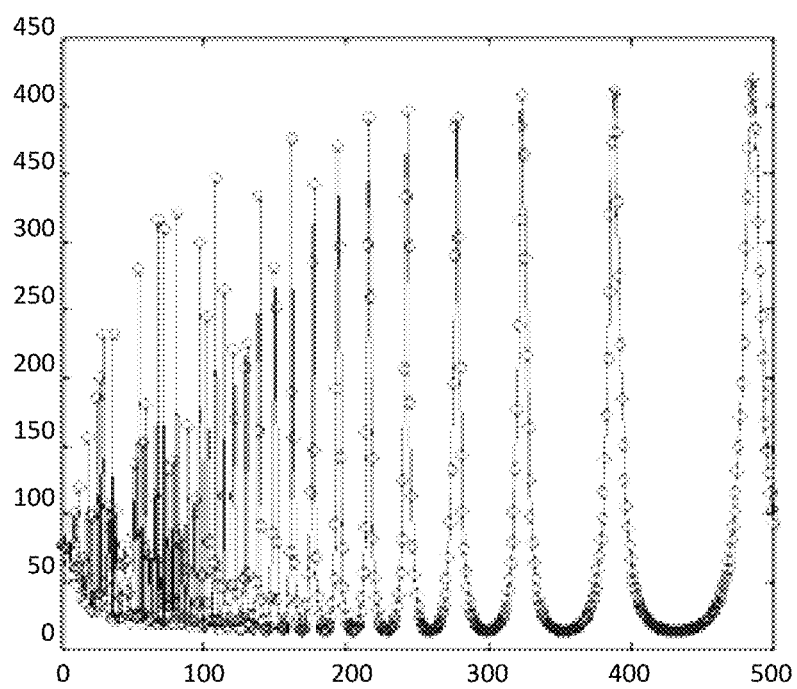
FIG. 17 shows the transform of the spectrum in function of the waveguide index in accordance with example embodiments.
Figure 18:
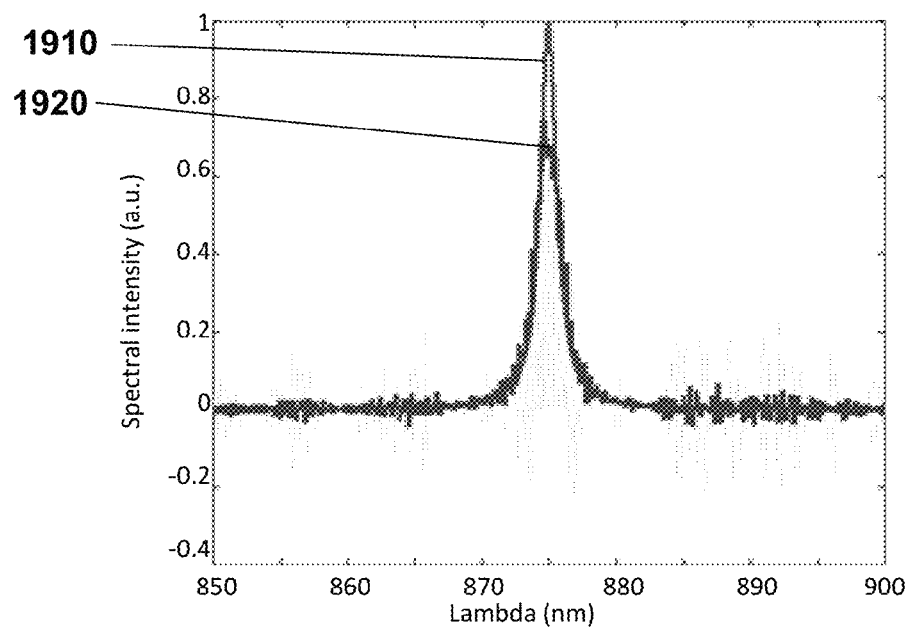
FIG. 18 shows an incoming spectrum and the reconstructed spectrum in accordance with example embodiments.
Figure 19:
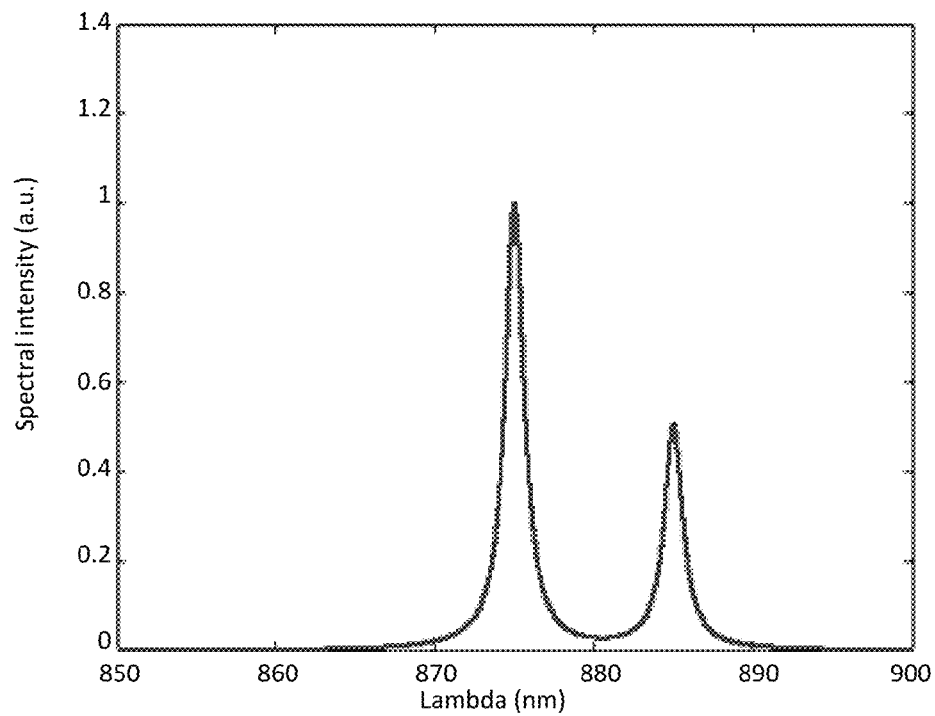
FIG. 19 shows an incoming spectrum as can be processed in a system according to example embodiments.
Figure 20:
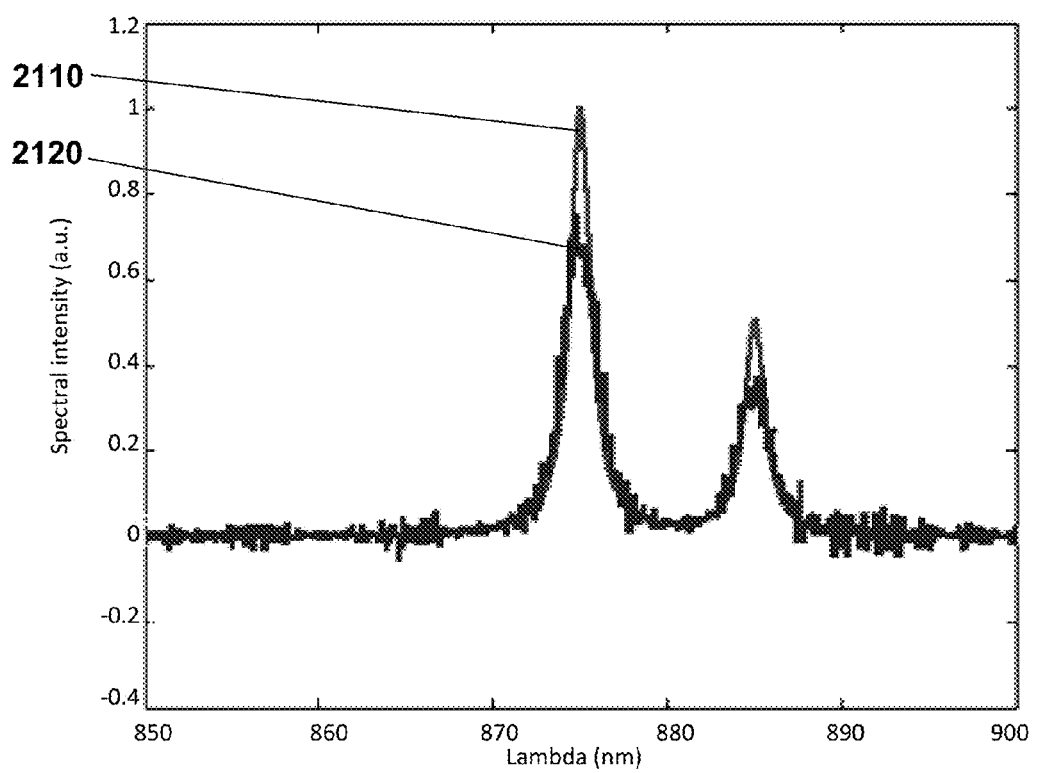
FIG. 20 shows an incoming spectrum and the reconstructed spectrum in accordance with example embodiments.

FIG. 13, FIG. 14, and FIG. 15 show the transmission ($T_j(\lambda)$) of a waveguide in an optical system according to an embodiment. A Fabry-Perot type spectrally dependent transmission system 140 is assumed. The length of the waveguide is 0.03 mm in case of FIG. 13, 0.1 mm in case of FIG. 14 and 0.5 mm in case of FIG. 15. The figures show the transmission in function of the wavelength. The transmission is measured at the outcoupling grating 230. FIG. 16 shows the incoming spectrum. The spectral intensity $S(\lambda)$ is shown in function of the wavelength. FIG. 17 shows the transform of the spectrum response as a function of the waveguide index when the same spectrum is inserted in every waveguide. FIG. 17 shows:

$$r_j = \int T_j(\lambda) S(\lambda) d\lambda$$

wherein j is the waveguide index, S is the incoming spectrum, and $T_j$ is the transmission of waveguide j. In some embodiments, the input spectrum may be reconstructed based on the measurement results. The spectrum may be reconstructed using a least square fit. Such a reconstruction is shown in FIG. 18. FIG. 18 shows the input spectrum 1910 and shows the reconstructed spectrum 1920. The spectrum is reconstructed based on the measurement result shown in FIG. 17. In some embodiments, a complete reconstruction of the input spectrum is not required (e.g. for the estimation of a glucose concentration). FIG. 19 shows an input spectrum with a double peak. One at 885 nm and one at 875 nm. FIG. 20 shows the input spectrum 2110 as well as the reconstructed spectrum 2120.

By decreasing the length of the spectrally dependent transmission system to 50 µm a spectrometer chip 130 with a height of 20 mm can comprise 200 lines instead of 40. By increasing the number of waveguides with a factor 5, also the chip étendue is increased with a factor 5 to 0.58 mm². Some embodiments, that by decreasing the height of the spectrometer chip 130 allow the matching to be improved. In an embodiment comprising 4000 waveguides per spectral response characteristic all 4000 waveguides need to be matched since the response will be added to obtain a SNR>1.

In some embodiments a first rejection filter 140 may be present between the collimator 110 and the beam shaper 120. The first rejection filter may for example be provided for rejecting an excitation beam used for optically exciting a region of interest at one wavelength, whereas a radiative response at another wavelength is expected. In particular embodiments, the optical density of the first rejection filter may be above 6 for wavelengths between 675 nm and 830 nm. In the embodiment of FIG. 1 the light coming from the collimator 110 enters the rejection filter 140. The light coming from the rejection filter 140 enters the wedge 120 at the wedge entrance area 122 and leaves the wedge at the wedge exit area 124. The wedge entrance area 122 has an area of 30 mm². The étendue of the light is 1.2 mm². The light entering the collimator has an angular spread of 10.5° and a photon flux of 0.4×10⁸ photons/sec.

Figure 2:
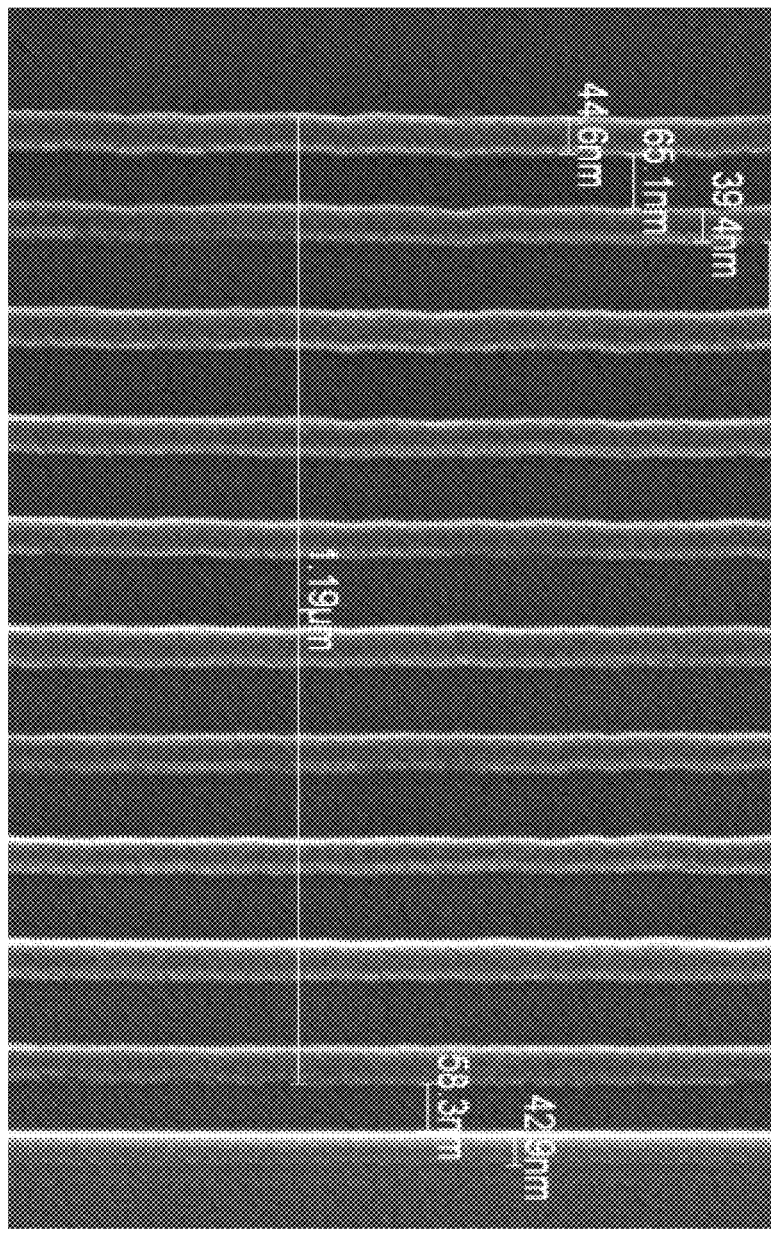
FIG. 2 shows a TEM image of a second rejection filter in accordance with example embodiments.
Figure 3:
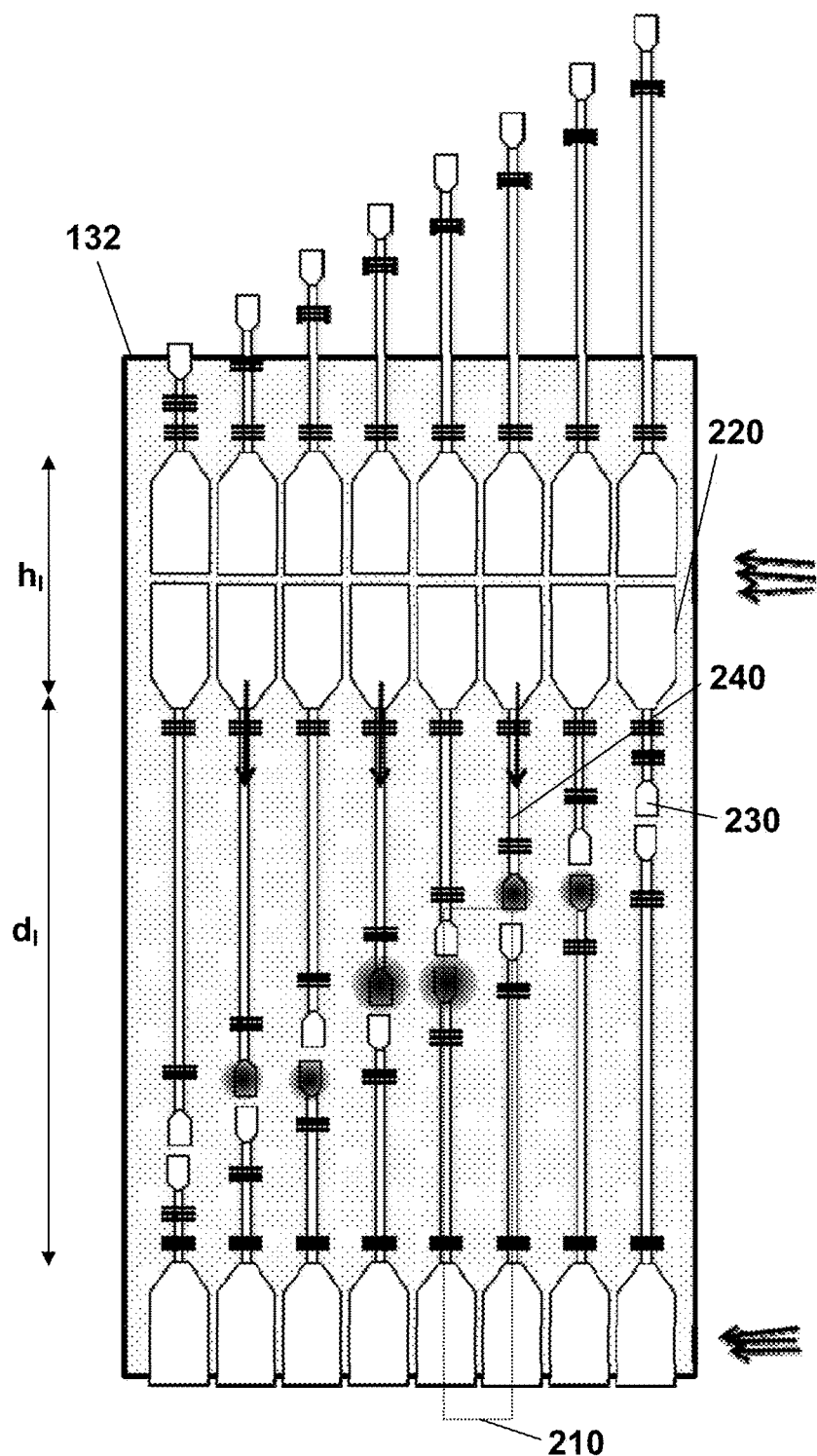
FIG. 3 shows a schematic drawing of a spectrometer chip in accordance with example embodiments.

In some embodiments, a second rejection filter also may be present between the beam shaper 120 and the spectrometer chip 130. In some embodiments, the second rejection filter may be an on-chip long pass rejection filter using multilayer $SiO_2$/a-SiC:H. The optical density of the second rejection filter may be above 3. An embodiment thereof optimized for rejection at 532 nm is shown in FIG. 2.

The number of filters is not limited to 1 or 2. In some embodiments a third rejection filter also may be implemented inherently by using a single mode waveguide with a Bragg grating. The optical density of the third rejection filter may be above 1. Also a fourth rejection filter is present between the photonic chip and the imager/detector. The optical density of the fourth rejection filter may be above 4.

In some embodiments, the overall optical density thus obtained may be above 9.

The optical system 100, according to some embodiments, can be used in several types of products. Below is described how it is used as a glucose sensor. When used as a glucose sensor the following signal to noise ratios are to be considered:

$SNR_{peak, \, glucose}$: the signal to noise ratio of the Raman spectral signal for glucose in deionized water measured at strong glucose Raman peaks, for example the 1126 cm⁻¹ peak being the glucose peak providing the strongest signal. In this case no strong fluorescence or Raman background is present.

$SNR_{peak, \, skin}$: the signal to noise ratio of the Raman spectral signal for glucose in skin measured at strong glucose Raman peaks. In this case strong background fluorescence and other Raman signals lead to large shot noise.

$SNR_{system}$: the signal to noise ratio of a glucose concentration measurement after analysis of spectrum. This value is higher than the $SNR_{peak,skin}$ because information from multiple peaks is combined.

The signal to noise ratio assuming only glucose in water can be estimated as follows:

$$SNR_{peak,skin} = \frac{P_{glucose} \cdot t_{int} \cdot \eta_{IC} \cdot \eta_{det}}{\sqrt{P_{glucose} \cdot t_{int} \cdot \eta_{IC} \cdot \eta_{det}}}$$

wherein:

$P_{glucose}$ is the glucose spectrum $\eta_{ic}$ is the incoupling efficiency being the overall incoupling efficiency of the optical system, $\eta_{det}$ is the detector efficiency and t is the integration time.

Figure 4:
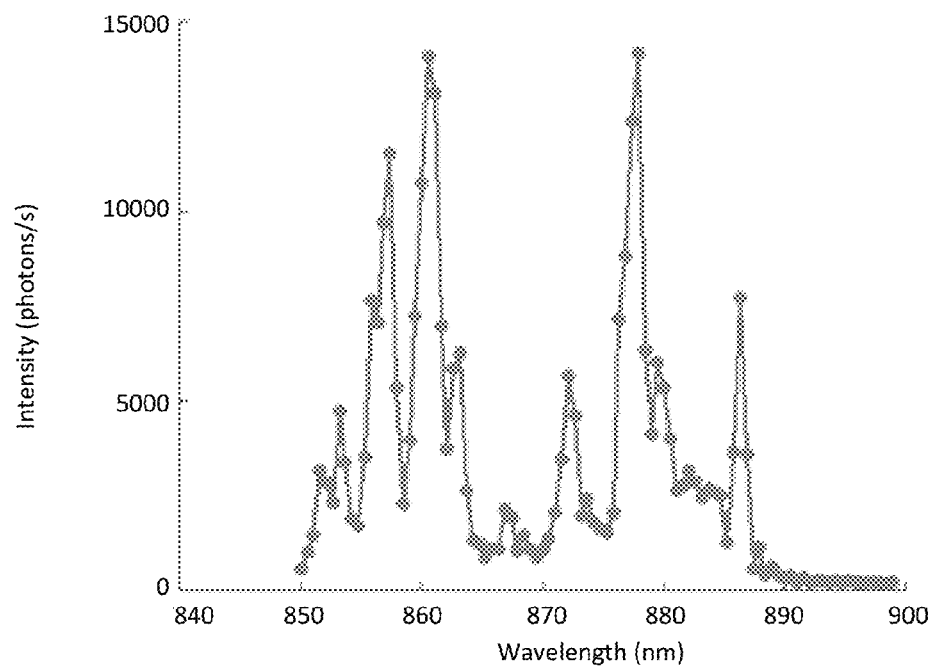
FIG. 4 shows an example of a glucose spectrum as can be obtained with Raman spectroscopy as can be used in example embodiments.

An example of the glucose spectrum multiplied with the detector efficiency is illustrated in FIG. 4.

The signal to noise ratio of the Raman spectral signal for glucose in skin assuming a background signal that is 1000 times stronger than the noise signal in DI water can be estimated as follows:

$$SNR_{peak,skin} = \frac{P_{glucose} \cdot t_{int} \cdot \eta_{IC} \cdot \eta_{det}}{\sqrt{P_{glucose} \cdot t_{int} \cdot \eta_{IC} \cdot \eta_{det} + P_{background}}}$$

wherein:

$P_{background}$=1000 max ($P_{glucose}$).

Figure 5:
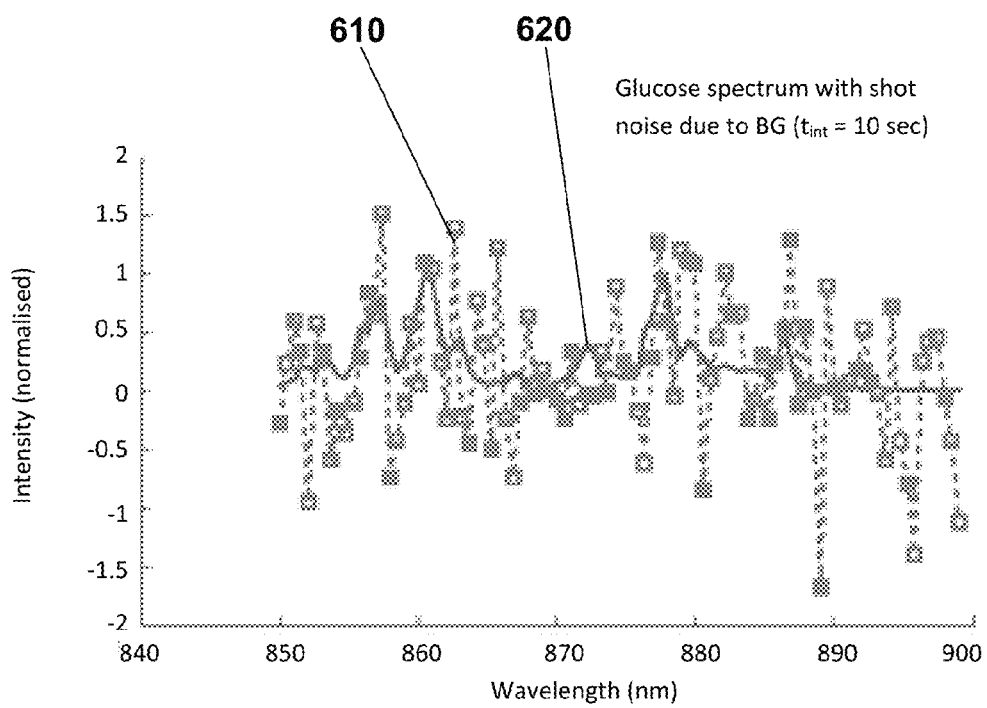
FIG. 5 shows a glucose spectrum and a measured glucose spectrum including shot noise measured using an optical system during a 10 sec integration time in accordance with example embodiments.
Figure 6:
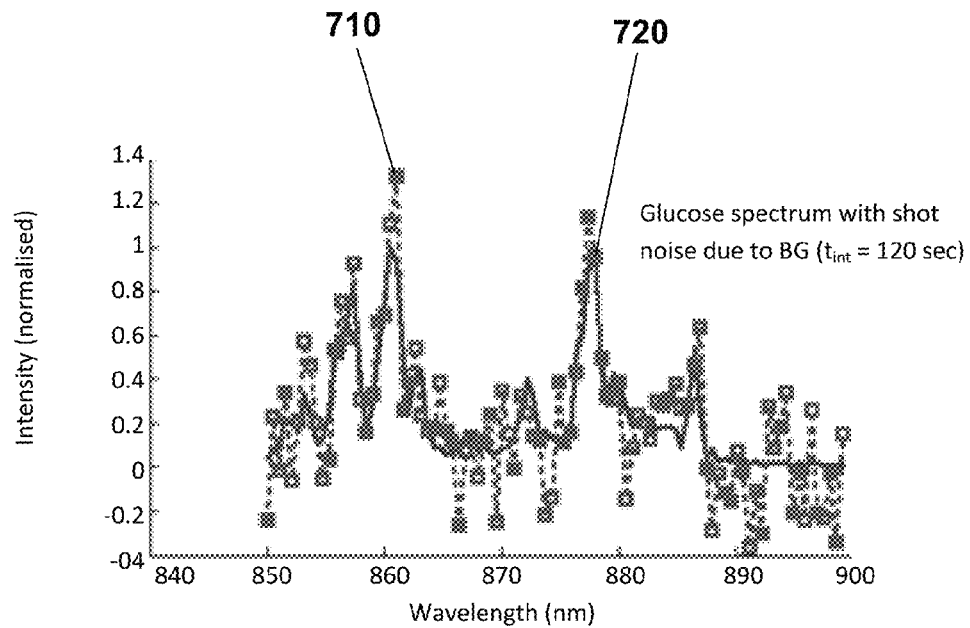
FIG. 6 shows a glucose spectrum and a measured glucose spectrum including shot noise measured using an optical system during a 120 sec integration time in accordance with example embodiments.

FIG. 5 shows the measured spectrum 610 after an integration time of 10 seconds and the spectrum without noise 620. FIG. 6 shows the measured spectrum 710 after an integration time of 120 seconds and the spectrum without noise 720. Given a glucose spectrum $P_{glucose} \times \eta_{det}$ a $SNR_{peak, skin}$ of 1.7 can be obtained after a 10 seconds integration time and a $SNR_{peak}$ skin of 6 can be obtained after a 120 seconds integration time.

Figure 7:
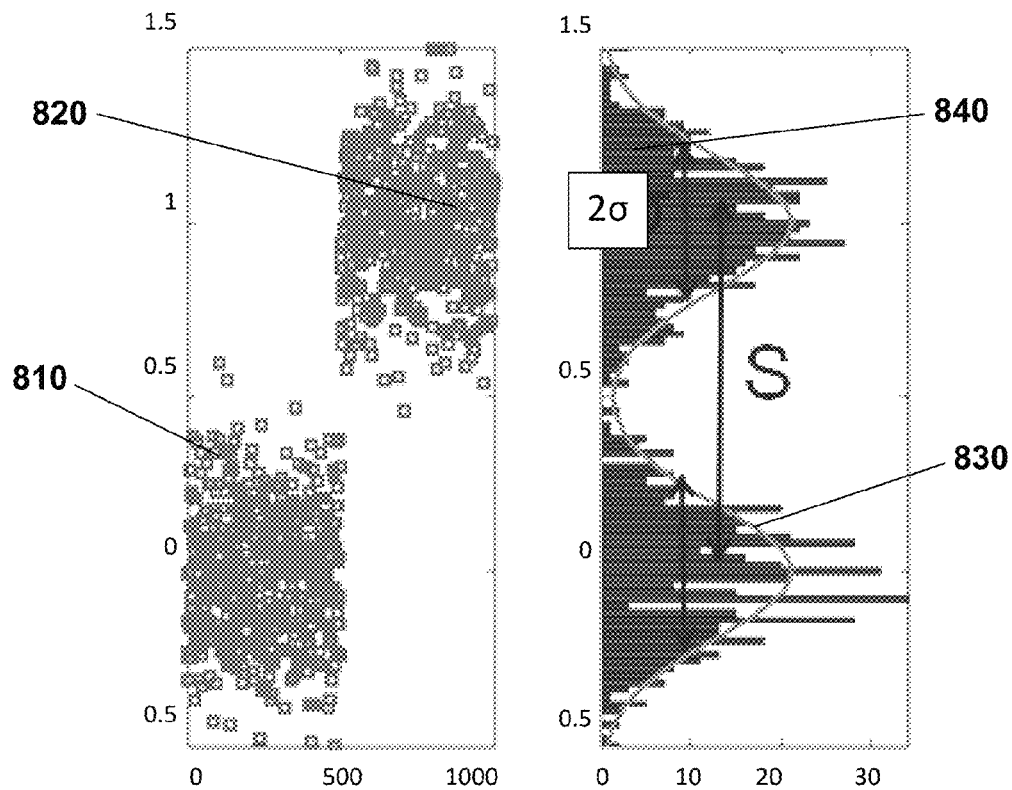
FIG. 7 shows a glucose histogram measured using an optical system during a 10 sec integration time accordance with example embodiments.
Figure 8:
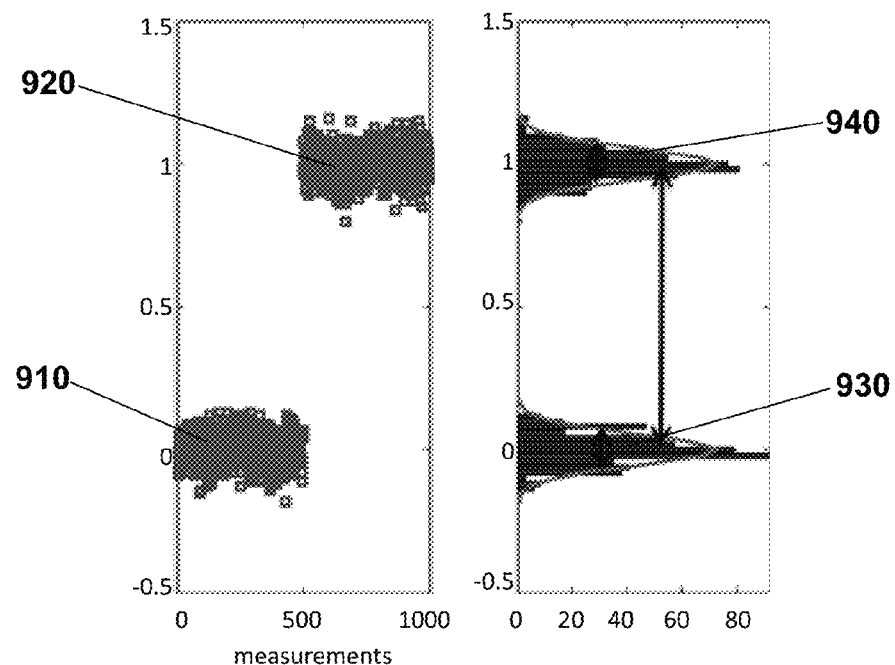
FIG. 8 shows a glucose histogram measured using an optical system during a 120 sec integration time accordance with example embodiments.

In some embodiments, the glucose signal is estimated by least square fitting the glucose spectrum with each of the measured spectra. When assuming a known and stable background an increased signal to noise ratio can be obtained. After a 10 seconds integration time the obtained $SNR_{system}$ is 4.0 instead of $SNR_{peak, skin}$ of 1.7. This is illustrated in FIG. 7. The estimated glucose concentration for a set of measurements on a sample without glucose is shown (810) as well as on a sample with 40 mg/dl of glucose (820). The histograms 830 and 840 are also shown. After a 120 seconds integration time the obtained $SNR_{system}$ is 13 instead of $SNR_{peak, skin}$ of 6. This is illustrated in FIG. 8. The estimated glucose concentration for a set of measurements on a sample without glucose is shown (910) as well as on a sample with 40 mg/dl of glucose (920). The histograms 930 and 940 are also shown. 500 fits were done without glucose (noise is seen as glucose contribution), and 500 fits with glucose at 40 mg/dl. 40 mg/dl is the minimum physiological concentration of glucose. The $SNR_{system}$ is expected to scale with the sqrt(number of strong peaks=6)~2.5. This corresponds with the results shown in FIG. 7 and FIG. 8 when applying the following formula:

$$SNR_{system} = \frac{S}{\sqrt{2}\,\sigma}$$

wherein S and σ are as shown in the FIG. 7.

Figure 9:
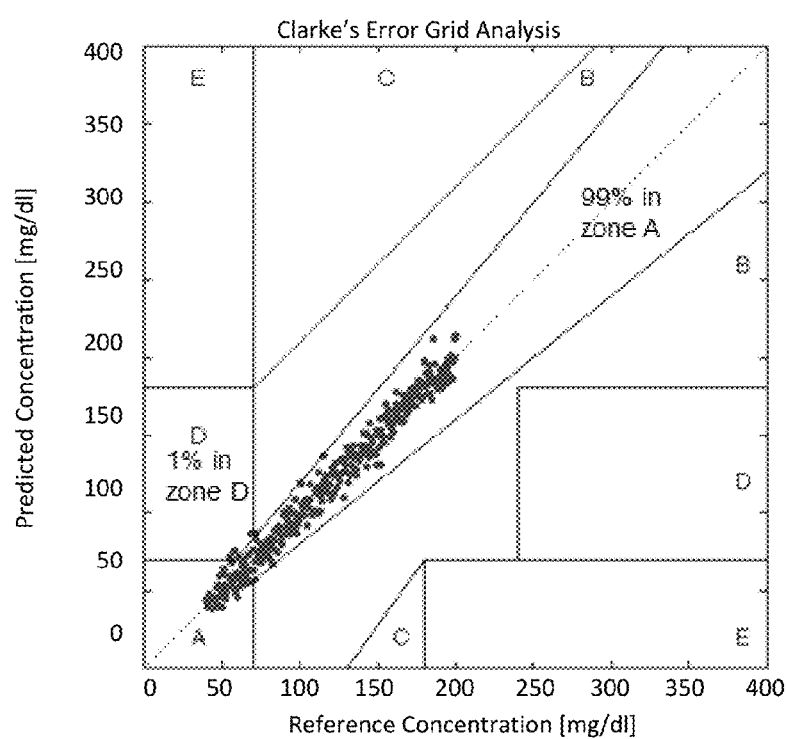
FIG. 9 shows a Clarke error grid representing measurements (10 seconds integration time) in accordance with example embodiments.
Figure 10:
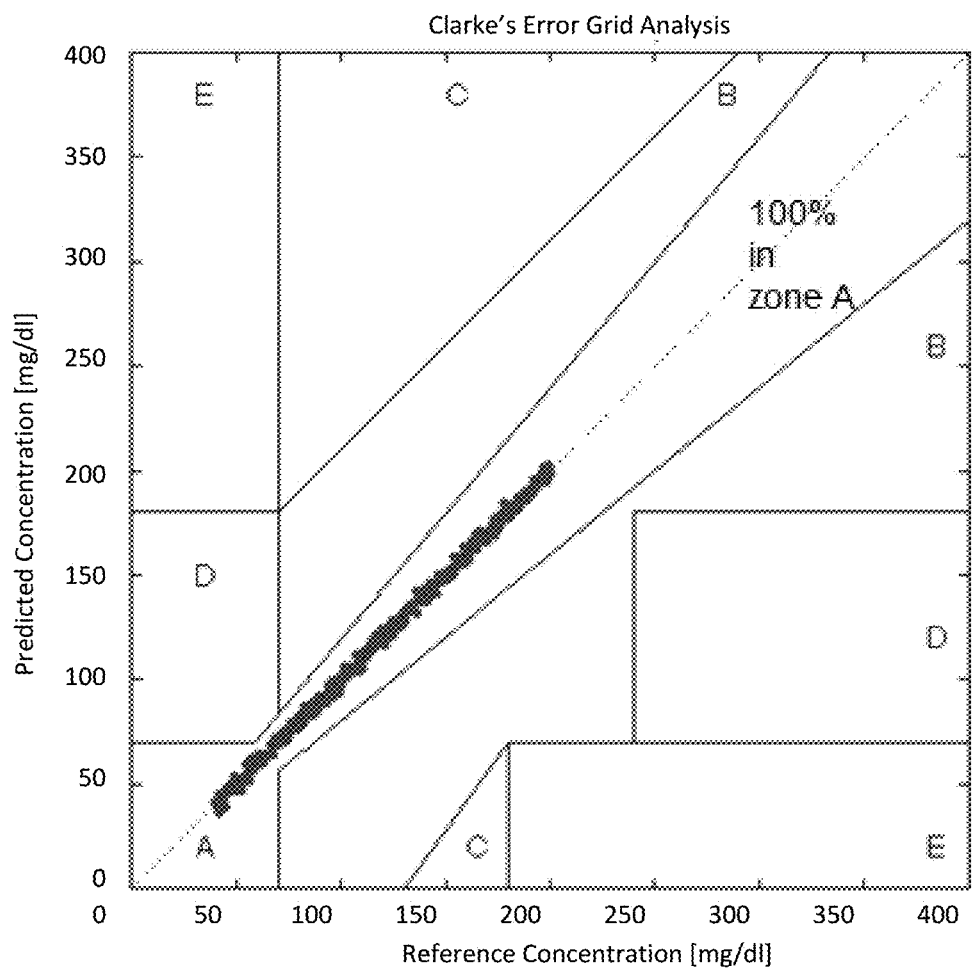
FIG. 10 shows a Clarke error grid representing measurements (120 seconds integration time) in accordance with example embodiments.

FIG. 9 and FIG. 10 show a Clarke error grid for the $SNR_{system}$ after a ten seconds integration time and 120 seconds integration time respectively. The incoupling efficiency $\eta_{ic}$ of both is equal to 2%, the detector efficiency $\eta_{det}$ is equal to 30%. A background signal 1000 times stronger than the glucose signal is assumed. According to the FDA guidance 95% of the measurements should fall in zone A, less than 5% should fall in zone B, and 0% should fall in zones C, D or E. The $SNR_{system}$ corresponding with FIG. 9 is equal to 3.9 and the $SNR_{system}$ corresponding with FIG. 10 is equal to 13. From the graphs it can be concluded that a $SNR_{system} > 4$ at the lowest physiological concentration of (40 mg/dl) is sufficient for glucose concentration. Some embodiments allow this signal to noise ratio to be obtained.

Figure 11:
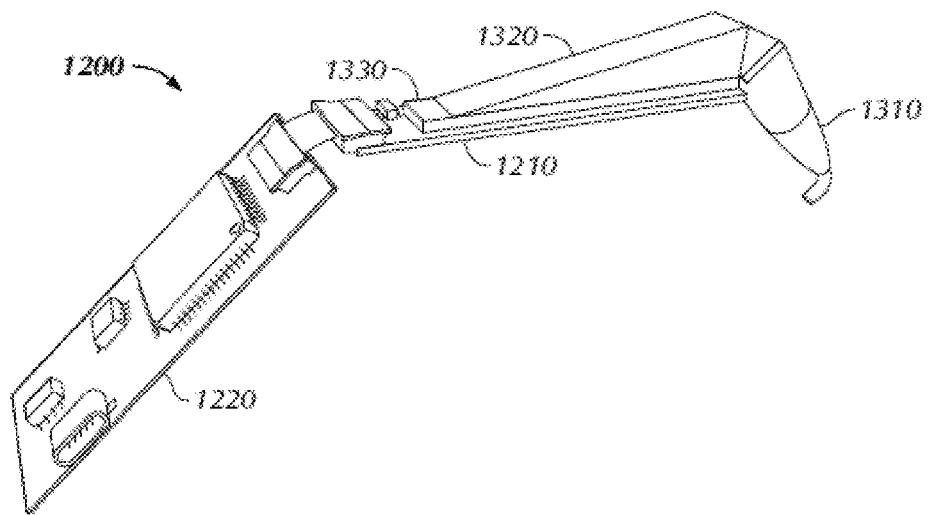
FIG. 11 provides a schematic 3D drawing of a detector system in accordance with example embodiments.

In a second aspect, the present invention relates to a detector system 1200. The detector system 1200 comprises an optical system 100 as indicated above being part of or being mounted on an optical printed circuit board 1210, including the optical part of the spectrometer. The detector system 1200 moreover comprises a read-out printed circuit board 1220 for reading out the optical signal received from the optical part of the spectrometer described in the first aspect. The read-out printed circuit board 1220 is connected with the optical printed circuit board 1210. The read-out printed circuit board 1220 digitizes the optical signal coming from the optical system 100 and/or processes the digitized result. An embodiment thereof is shown in FIG. 11.

Figure 12:
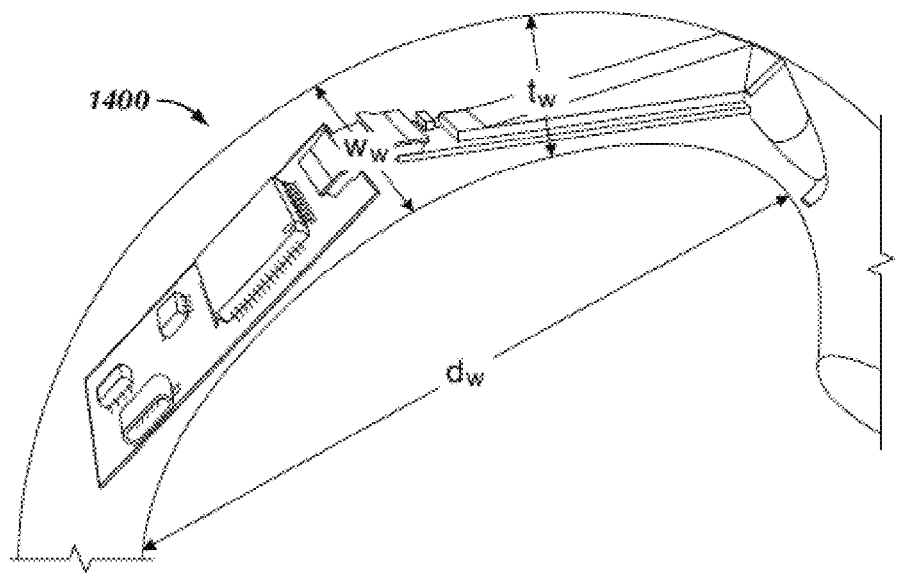
FIG. 12 provides a schematic 3D drawing of a detector system comprising a wrist band in accordance with example embodiments.

In some embodiments, the detector system 1200 comprising a wristband 1310. The optical system 100 and the read-out printed circuit board 1220 are integrated in the wristband 1310. In the embodiment illustrated in FIG. 12 the dimensions $d_w$, $t_w$, and $w_w$ are indicated. These dimensions may be as follows: $d_w = 6.5$ cm, $t_w = 7.4$ mm, and $w_w = 14$ mm. Due to the small thickness of the optical system, the wristband can be limited in height, resulting in a high degree of wearability.

In a third aspect, the present invention also relates to an optical radiation guiding system comprising a collimator and beam shaper as described in the first aspect, without the optical part of the spectrometer being present. Such an optical radiation guiding system thus may be a separate component. Features thereof may be as described in the first aspect.

In the following aspects the RAMAN spectrometer in the associated embodiments corresponds with an optical system according to the previous aspects of previously described embodiments.

In a fourth aspect of the disclosure, an integrated circuit for performing spectroscopy on tissue is presented. The device comprises: a first optical unit comprising: a RAMAN spectrometer; an OCT spectrometer; an interferometer optically coupled to the OCT spectrometer; and a light coupler, positioned to couple scattered and reflected light from illuminated tissue into the RAMAN and OCT spectrometer; and an imaging region optically coupled to the RAMAN and OCT spectrometer. According to an embodiment of the disclosure, the integrated circuit further comprises at least a second optical unit, wherein the imaging region is optically coupled to the RAMAN and OCT spectrometer of each optical unit. According to an embodiment of the disclosure, the first optical unit further comprises an IR spectrometer optically coupled to the light coupler; and further comprising an infrared imaging region optically coupled to the IR spectrometer.

In a fifth aspect of the disclosure, an integrated circuit for performing spectroscopy on tissue is presented. The device comprises: a first optical unit comprising: a RAMAN spectrometer; an IR spectrometer; a light coupler, positioned to couple scattered and reflected light from illuminated tissue into the RAMAN and IR spectrometer; an imaging region optically coupled to the RAMAN spectrometer; and an infrared imaging region optically coupled to the IR spectrometer. According to an embodiment of the disclosure, the integrated circuit further comprises at least a second optical unit; wherein the imaging region is optically coupled to the RAMAN spectrometer of each optical unit; and wherein the infrared imaging region is optically coupled to the IR spectrometer of each optical unit. According to an embodiment of the disclosure, the first optical unit further comprises: an OCT spectrometer optically coupled to light coupler; and an interferometer optically coupled to the OCT spectrometer; and wherein the imaging region is optically coupled to the OCT spectrometer. According to an embodiment of the disclosure, the integrated circuit further comprises at least a second optical unit; wherein the imaging region is optically coupled to the RAMAN and OCT spectrometer of each optical unit; and wherein the infrared imaging region is optically coupled to the IR spectrometer of each optical unit. According to an embodiment of the disclosure, the integrated circuit further comprises at least one optical waveguide distributor for distributing a light beam of a light source on the integrated circuit thereby allowing simultaneous illumination of different locations of tissue. According to an embodiment of the disclosure, the integrated circuit further comprises at least one through-hole thereby allowing illumination of tissue through the integrated circuit. According to an embodiment of the disclosure, the integrated circuit further comprises at least one rejection filter located to allow, when in operation, only scattered light reaching the RAMAN spectrometer. According to an embodiment of the disclosure, the integrated circuit comprises a plurality of active electronic component layers thereby forming a three-dimensional integrated circuit wherein each active electronic component layer comprises the first optical unit or the at least one second optical unit. The integrated circuit may be a 3D (stacked) integrated circuit comprising different layers, each layer comprising an optical unit. According to an embodiment of the disclosure, the light coupler of the first or the at least one second optical unit of each active electronic component layer is configured to couple light with a different wavelength into the RAMAN spectrometer. Each light coupler of an optical unit present in a layer of the 3D integrated circuit may be configured to couple light with a specific wavelength in a spectrometer. The wavelength ranges of different light couplers may be adjacent to allow in coupling of light with wavelengths falling within a specific wavelength range. According to an embodiment of the disclosure, one or more photodiodes of the imaging region comprise a spectral filter for spectrally resolving RAMAN scattered light. At least one photodiode in the imaging region, which may be present in an active electronic component layer of the integrated circuit, may comprise a spectral filter. Different photodiodes of the imaging region may comprise different spectral filters.

In a sixth aspect of the disclosure, a wearable system for non-invasive measuring of the concentration of an analyte in tissue is presented. The system comprising: an integrated circuit according to an embodiment of the disclosure; a first light source optically coupled to the integrated circuit and configured to emit a laser beam for performing Raman spectroscopy; a second light source optically coupled to the integrated circuit and configured to emit a broadband light beam for performing OCT spectroscopy or IR spectroscopy; read-out electronics electrically coupled to the integrated circuit and configured to read out and correlate spectroscopic data from the RAMAN and IR spectrometer or from the RAMAN and OCT spectrometer and to determine the concentration of an analyte using the correlated spectroscopic data. According to an embodiment of the disclosure, the system further comprises a third light source optically coupled to the integrated circuit and configured to emit a broadband light beam for performing IR spectroscopy or OCT spectroscopy; and wherein the read-out electronics is further configured to read out and correlate spectroscopic data from the RAMAN, OCT and IR spectrometer and determine the concentration of an analyte using the correlated spectroscopic data.

According to an embodiment of the disclosure, the second light source is a low coherent light source or a very wide bandwidth source and the third light source is low coherent light source or a very wide bandwidth source.

According to an embodiment of the disclosure, the system further comprises at least one optical reflector adapted to couple light from a light source in the integrated circuit.

According to an embodiment of the disclosure, the tissue is skin tissue and the system is completely packaged in a wearable casing and the wearable casing is adapted to press the integrated circuit against the skin tissue of an individual when worn thereby allowing scattered and reflected light from illuminated skin tissue to be received by the integrated circuit. According to an embodiment of the disclosure, the wearable casing is a wristband, the size of the wristband being adaptable to allow pressing of the integrated circuit against the skin of an individual when worn. According to an embodiment of the disclosure, the wearable casing is a watch comprising a watch strap, the size of the watch strap being adaptable to allow pressing of the integrated circuit against the skin of an individual when worn.

In a seventh aspect of the disclosure, a method for non-invasive measuring of the concentration of analyte in tissue using the wearable system is presented. The method comprises: simultaneously obtaining spectra of Raman scattered light at different locations of the tissue; obtaining an optical model of the tissue; correlating the obtained spectra of Raman scattered light with the obtained optical model; determining the concentration of the analyte using the correlated data.

According to an embodiment of the disclosure, obtaining an optical model of the tissue comprises determining thicknesses and optical properties of different layers of the tissue. According to an embodiment of the disclosure, the tissue is skin tissue and obtaining an optical model of the tissue comprises obtaining a skin model of skin tissue underneath the sensor, the skin model comprising information on thickness and optical properties of different layers of the skin tissue. According to an embodiment of the disclosure, the skin model further comprises information on the refractive index of interstitial fluid and blood in the skin tissue. According to an embodiment of the disclosure, the analyte is glucose. According to an embodiment of the disclosure, obtaining an optical model of the tissue is done using IR spectroscopy and/or using OCT spectroscopy. According to an embodiment of the disclosure, simultaneously obtaining spectra of Raman scattered light of the tissue at different locations and obtaining an optical model of the tissue is performed simultaneously.

In an eighth aspect of the disclosure, the system may be used for measuring the concentration of glucose in living tissue.

The invention claimed is:

1. An optical system configured to characterize a radiation beam, the optical system comprising:
   an optical radiation guiding system, comprising:
      a collimator configured to collimate the radiation beam into a collimated radiation beam; and
      a beam shaper configured to distribute power of the collimated radiation beam over a discrete number of line shaped fields, wherein a spectrum of the collimated radiation beam entering the beam shaper is delivered to each of the discrete number of line shaped fields; and
   a spectrometer chip, wherein the spectrometer chip is configured to process the spectrum of the collimated radiation beam in each of the discrete number of line shaped fields coming from the beam shaper.

2. The optical system according to claim 1, wherein the beam shaper has a wedge shape.

3. The optical system according to claim 2, wherein the collimator and the beam shaper are arranged so that the beam shaper can receive radiation via a wedge entrance area, wherein the wedge entrance area is a short side of the wedge shape.

4. The optical system according to claim 2, wherein the beam shaper is shaped so that radiation incident orthogonally to a wedge entrance area is guided to a wedge exit area without first being reflected from another surface of the wedge shape.

5. The optical system according to claim 1, wherein at least part of the collimator has a 3D parabolic shape.

6. The optical system according to claim 1, wherein the collimator has an entrance point and is shaped so as to fold an irradiation beam between the entrance point and an output of the collimator.

7. The optical system according to claim 1, wherein the beam shaper comprises an exit area for directing the collimated radiation beam to the discrete number of line shaped fields, and wherein the exit area has a waved or stepped pattern.

8. The optical system according to claim 7, wherein the waved or stepped pattern comprises a plurality of first segments and a plurality of second segments, wherein the plurality of second segments interconnects the plurality of first segments, and wherein neighboring first segments are positioned at a distance shorter than a length of the first segments and oriented substantially parallel with an orthogonal direction to an entrance area of the beam shaper.

9. The optical system according to claim 8, wherein the second segments are curved.

10. The optical system according to claim 1, wherein the spectrometer chip comprises a plurality of detection channels, each detection channel comprising:
 an incoupling grating;
 an outcoupling grating; and
 a spectrally dependent transmission system, wherein the incoupling grating is coupled with the outcoupling grating through the spectrally dependent transmission system, and wherein the incoupling gratings of different detection channels are arranged on a discrete number of lines.

11. The optical system according to claim 10, wherein the spectrally dependent transmission system is a Fabry-Perot system.

12. The optical system according to claim 1, wherein a first rejection filter is present between the collimator and the beam shaper, and wherein the first rejection filter is configured to reject an excitation radiation.

13. The optical system according to claim 1, wherein the optical system is integrated in a wristband.

14. A glucose sensor configured to characterize a radiation beam, the glucose sensor comprising:
 an optical radiation guiding system, comprising:
  a collimator configured to collimate the radiation beam into a collimated radiation beam; and
  a beam shaper configured to distribute power of the collimated radiation beam over a discrete number of line shaped fields, wherein a spectrum of the collimated radiation beam entering the beam shaper is delivered to each of the discrete number of line shaped fields; and
 a spectrometer chip, wherein the spectrometer chip is configured to process the spectrum of the collimated radiation beam in each of the discrete number of line shaped fields coming from the beam shaper.

15. The glucose sensor according to claim 14, wherein the beam shaper has a wedge shape.

16. The glucose sensor according to claim 15, wherein the collimator and the beam shaper are arranged so that the beam shaper can receive radiation via a wedge entrance area, wherein the wedge entrance area is a short side of the wedge shape.

17. The glucose sensor according to claim 15, wherein the beam shaper is shaped so that radiation incident orthogonally to a wedge entrance area is guided to a wedge exit area without first being reflected from another surface of the wedge shape.

18. The glucose sensor according to claim 14, wherein at least part of the collimator has a 3D parabolic shape.

19. The glucose sensor according to claim 14, wherein the collimator has an entrance point and is shaped so as to fold an irradiation beam between the entrance point and an output of the collimator.

20. A method of characterizing a radiation beam using an optical system, comprising:
 collimating, by a collimator of an optical radiation guiding system of the optical system, the radiation beam into a collimated radiation beam;
 distributing, by a beam shaper of the optical radiation guiding system of the optical system, power of the collimated radiation beam over a discrete number of line shaped fields, wherein a spectrum of the collimated radiation beam entering the beam shaper is delivered to each of the discrete number of line shaped fields; and
 processing, by a spectrometer chip of the optical system, the spectrum of the collimated radiation beam in each of the discrete number of line shaped fields coming from the beam shaper.

* * * * *